United States Patent
Walter et al.

(10) Patent No.: US 7,875,266 B2
(45) Date of Patent: Jan. 25, 2011

(54) USE OF DI-OR OLIGOSACCHARIDE POLYESTER IN HAIR STYLING PRODUCTS

(75) Inventors: Andrea Walter, Plochingen (DE); Susanne Birkel, Darmstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 760 days.

(21) Appl. No.: 11/607,225

(22) Filed: Dec. 1, 2006

(65) Prior Publication Data

US 2007/0184007 A1    Aug. 9, 2007

(51) Int. Cl.
*A61Q 5/06* (2006.01)
(52) U.S. Cl. .................................... 424/70.11
(58) Field of Classification Search ........................ None
See application file for complete search history.

(56) References Cited

U.S. PATENT DOCUMENTS

| 6,936,264 B2* | 8/2005 | Glenn et al. ................. 424/401 |
| 2005/0163738 A1* | 7/2005 | Loifenfeld et al. ......... 424/70.1 |

OTHER PUBLICATIONS

International Cosmetic Ingredient Dictionary and Handbook, 10th Edition 2004, vol. 3, Section 3 "Colorants.", Sep. 2003.

* cited by examiner

*Primary Examiner*—Jyothsna A Venkat
(74) *Attorney, Agent, or Firm*—Angela K. Haughey; Laura R. Grunzinger

(57) ABSTRACT

The present invention relates to the use of fully esterified di- or oligosaccharide polyesters in hair styling products selected from hair styling waxes, hair styling creams, hair styling foam wax products, and hair styling spray wax products. Preferred saccharide polyesters are octaesters of sucrose and C8 to C30 fatty acids such as behenic acid and fatty acids derived from cotton seed oil.

1 Claim, No Drawings

USE OF DI- OR OLIGOSACCHARIDE POLYESTER IN HAIR STYLING PRODUCTS

FIELD OF THE INVENTION

The present invention relates to a method of treating hair comprising the use of hair styling products, the hair styling products comprising fully esterified di- or oligosaccharide polyester. The hair styling products are selected from the group consisting of hair styling waxes, hair styling creams, hair styling foam wax products, and hair styling spray wax products.

BACKGROUND OF THE INVENTION

Hair styling products are intended for helping to create individual hair styles and for temporarily holding them in place for a period of time. Hair styling wax products and styling cream products play an important role among styling products. They particularly find application in putting short to medium length hair in a fashionable hairstyle and impart hold, texture, and luster as well as stabilize, condition, and fix the hairstyle. They provide the hairstyle with shape and luster and frequently with a wet-look appearance. Application of wax containing hair styling products is usually based on the following principles. Solid products are removed with the fingers from suitable containers. Sprayable or foamable wax products are sprayed onto the hand. Creamy products can be squeezed out of a tube onto the hand. The product is distributed on the surface of the hand and the waxy ingredients are melted or at least considerably softened by the heat of the hand in combination with the shear energy of rubbing. It is possible to work the otherwise too hard wax into the hair because of this softening or melting. The wax is worked into the hair in a softened or more or less liquid state. Then it cools and again reaches its original solid or semi-solid consistency. It hardens and the hairdo obtained has stability and hold and frequently a wet-look appearance. Not all waxy materials are equally well suited for being used in hair styling wax products because of manifold requirements. The product should have a homogeneous consistency and should not crumble during application. The wax should not be too hard in order to be distributable on hand and hair but not too soft in order to provide enough hold and texture. It should provide gloss on hair but not form visible crumbs or visible white residues on the hair. One of the best suited waxes is carnauba wax. It is hard enough to give good hold and texture but can be softened to be good distributable especially when combined with softer waxes or oils. One disadvantage of carnauba wax is its unpleasant yellowish color. Waxes with a whiter color, e.g., hydrocarbon waxes are known but these waxes usually do not combine all of the performance benefits of carnauba wax.

It is a special challenge to formulate a hair styling wax product with improved whiteness or color brightness and which has at least similar or even better performance benefits as wax products containing carnauba wax, especially in view of product homogenity, distributability in the hand and on the hair, good hair texture, hair hold, hair shine and/or wet-look. It is an object of the present invention to provide hair wax products, which improve the hold, texture, and the shine of the hairstyle. Improving hair texture means to impart desirable surface characteristics to hair or to the hairdo. At the same time the product mass should have a pleasant, white appearance and be easily and satisfactorily processed and worked into the scalp hair without crumbling or forming visible residues and with an acceptable, not too high loading of the hair and with a smoother feel of the product itself and of the hair after application of the product.

SUMMARY OF THE INVENTION

It has now been found that high performance white hair styling wax products can be formulated by the use of fully esterified di- or oligosaccharide polyesters. The present invention is directed to a method of treating hair comprising the use of hair styling products, the hair styling products comprising fully esterified di- or oligosaccharide polyester. The hair styling products are selected from the group consisting of hair styling waxes, hair styling creams, hair styling foam wax products, and hair styling spray wax products. These and other features, aspects, and advantages of the present invention will become evident to those skilled in the art from a reading of the present disclosure.

DETAILED DESCRIPTION OF THE INVENTION

All percentages, parts, and ratios are based upon the total weight of the compositions of the present invention, unless otherwise specified. In case of aerosol products the amounts of ingredients of the base composition are based on the total weight of the base composition without propellant, unless otherwise specified. The propellant amount is based on the total weight of the composition including base composition and propellant. All such weights as they pertain to listed ingredients are based on the active level and, therefore, do not include solvents or by-products that may be included in commercially available materials, unless otherwise specified. All molecular weights as used herein are weight average molecular weights expressed as grams/mole, unless otherwise specified. Herein, "comprising" means that other steps and other ingredients which do not affect the end result can be added. This term encompasses the terms "consisting of" and "consisting essentially of." The compositions and methods of the present invention can comprise, consist of, and consist essentially of the essential elements and limitations of the invention described herein, as well as any of the additional or optional ingredients, components, steps, or limitations described herein. The terms "hydrophobic" as used herein, mean substances which are substantially water insoluble (e.g., less than 1% by weight at 25° C.), but soluble in an oil phase, with the solubility in an oil phase being higher than that in a water phase. The term "room temperature" as used herein, means 25° C. The term "wax" or "wax-like" as used herein, corresponds to the definition of "wax" in *Ullmanns' Encyclopedia for Industrial Chemistry,* 4th Edition, Volume 24, page 3. According to this definition wax substances are plastic at 20° C., solid to brittle, gross to fine crystalline, transparent to opaque, but not glassy, melting over 40° C. without decomposition. They have a comparatively low viscosity above their melting point, have a consistency and solubility that is comparatively temperature dependent and are polishable with a gentle pressure.

Di- or Oligosaccharide Polyesters

The di- or oligosaccharide polyesters can be liquid/oily or preferably solid/waxy at room temperature. The amounts of di- or oligosaccharide polyesters used in styling compositions can vary for example from about 0.01% to 60% by weight or preferably from about 0.1% to 30% by weight or from about 0.5% to 20% by weight or from about 1% to 15% by weight and can be adjusted to the requirements of the specific product type. Di- and oligosaccharides suitable for use herein include, for example, maltose, kojibiose, nigerose, cellobiose, lactose, melibiose, gentiobiose, turanose, rutinose, trehalose, sucrose, and raffinose. Preferred saccharides are di- and trisaccharides, most preferred are disaccharides, especially sucrose. The saccharide esters can be esters of the respective saccharide with a single type of acid or they can be mixed esters with different acids. Preferred are esters with fatty acids, especially with C8 to C30 fatty acids, more preferred with C10 to C26 or C12 to C22 fatty acids or with mixtures of these acids. Non-limiting examples of fatty acids are capric, caprinic, lauric, palmitic, margaric, stearic, ararchic, behenic, isomyristic, myristic, caprylic, linolic, linoleic, oleic, triacontanoic acid. Preferred are also fatty acid mixtures derived from vegetable oils like cotton seed oil or soya oil. Cotton seed oil for example is a mixture of triglycerids of predominantly linolic acid (about 45-58%), palmitic acid (21-27%), oleic acid (14-21%), and stearic acid (2-3%) from which the fatty acid mixture (cottonseed acids) can be obtained by hydrolysis.

The fully esterified saccharide esters can be used in combination with non-fully esterified saccharides. For example, a disaccharide octaester can be used together with the respective hepta or hexa esters, etc. Preferred sachcarides are disaccharides. Preferred disaccharide is sucrose. Commercial products typically are a mixture. The amount of octaester is preferably at least 70% by weight, for example, from about 70% to 80% of all disaccharide esters. The amount of hepta ester may be for example from about 20% to 30% and the amount of hexa, penta, and lower esters preferably each being below 1%. The sum of octa and hepta esters is preferably at least 95% of all esters and the sum of octa, hepta, and hexa esters is preferably at least 97% of all esters. Preferred are sucrose polyesters of behenic acid or cottonseed acids or soyate acids with the INCI-names Sucrose Polybehenate, Sucrose Polycottonseedate, and Sucrose Polysoyate, respectively. These substances are available under the trade names SEFA Behenate, SEFA Cottonate, and SEFA Soyate from Procter & Gamble Chemicals. Most preferred is sucrose polybehenate.

Oils

Preferred compositions additionally contain at least one hydrophobic oil that is liquid at room temperature and different from said oily saccharide polyesters. The term "liquid at room temperature" as used herein, means substances having a melting point below 25° C. and a boiling point above 25° C. Most preferred are low volatile oils with a boiling point, for example, of at least 200° C. or at least 250° C. or 300° C. The preferred amount of oil is at least 3% by weight, more preferred 5% to 60% or 10% to 50% by weight and comprises hydrophobic oil that is liquid at 25° C. and optionally dissolved lipophilic materials. The hydrophobic oils and the lipophilic materials of the oil phase can for example be selected from vegetable oils, animal oils, mineral oils, silicone oils, hydrocarbon oils, hydrogenated polyolefins, fatty alcohols with at least 8 carbon atoms including branched alcohols such as guerbet alcohols, oils from fatty acids and polyols (especially triglycerides), oils from fatty acids and monohydric C1- to C30-alcohols (preferred C3- to C22-alcohols) and mixtures of said hydrophobic oils. Non-limiting hydrophobic oils are for example cyclic paraffins, parrafin oils, isoparaffin oils, polydecene, mineral oil, isohexadecane, dodecane, isoeicosane, liquid polydimethylsiloxane, cyclotetrasiloxane, cyclopentasiloxane, phenyltrimethicone, isocetylpalmitate, isopropylmyristate, isopropylpalmitate, isopropylstearate, octylisostearate, octylcocoate, octylpalmitate, octyidodecylmyristate, caprylic/capric triglyceride, butyloctanol, hexyloctanol, butyldecanol, hexyldecanol, octyidodecanol, hexyldecanol, stearylheptanoate, isohexyldecanoate, isodecyloctanoate, dibutyladipate, dicaprylether, C12-15-alkylbenzoate, hydrogenated polyisobutene, squalane, squalene, native oils such as jojoba oil, olive oil, sunflower oil, soja oil, peanut oil, rape seed oil, sweet almond oil, palm-oil, coconut oil, castor oil, hydrogenated castor oil, wheat germ oil, grape seed oil, safflower oil, evening primrose oil, macedemia nut oil, corn oil, avocado oil, lanolin oils and similar oils. Especially preferred oil compounds are hydrocarbon oil such as mineral oil (e.g., paraffinum liquidum) and branched C8 to C30 alkyl alcohols. Silicone oils include polydimethylsiloxanes, phenylated silicones, polyphenylmethylsiloxanes, phenyltrimethicones, poly-C1 to C20-alkylsiloxanes, and alkylmethylsiloxanes.

Waxes

The hair styling product according to the invention comprises a composition which additionally can contain waxes or wax-like substances different from said waxy saccharide polyesters. The amount of additional waxes is preferably from about 1% to 60% by weight or from about 5% to 50% by weight. These waxes include animal, vegetable, mineral and synthetic waxes, solid paraffins, petrolatum (Vaseline®), ozocerite, ceresin, montan wax, Fischer-Topsch waxes, polyolefin waxes, such as polybutene, bees wax, wool wax and its derivatives, such as wool wax alcohols, candelilla wax, carnauba wax, japan wax, hardened fats, fatty acid esters and fatty acid glycerides with solidification points above 40° C., polyethylene waxes, and silicone waxes. The waxes or wax-like substances have a solidification point above 40° C., preferably above 55° C. The needle penetration number (0.1 mm, 100 g, 5 s, 25° C.; according to DIN 51 579) is preferably in a range of 2 to 70, especially from 3 to 40. Preferably at least one wax is present in the composition of the invention, which has a needle penetration point which is less than 40, especially preferably less than 20. Ceresine wax with a needle penetration point of less than 20 or beeswax or their mixtures are especially preferred.

Emulsifiers

Preferred embodiments of the invention additionally include at least one emulsifier, in order to improve the washability of the composition from the hair and to further improve the performance benefits. The emulsifiers are preferably contained in an amount of from about 0.5% to 20% by weight, especially preferably from about 3% to 15% by weight. Preferred emulsifiers are selected from the group of non-ionic and anionic surfactants. In a particularly preferred embodiment the emulsifiers have a wax-like consistency and a liquifying point over 25° C.

Nonionic emulsifiers are, for example:

alkoxylated fatty alcohols such as C8- to C30- or preferably C8- to C22-alcohols, alkoxylated fatty acids or alkoxylated fatty acid glycerides such as C12 to C22-fatty acids, alkoxylated alkylphenols (e.g., alkyl groups with 8 to 15 carbon atoms); typical degrees of ethoxylation being from 2 to 100 or 4 to 30 and typical degrees of propoxylation being from 1 to 5;

C8 to C30-, preferably C12- to C22-fatty acid glycerolmono- or diester, ethoxylated with from 1 to 30 mole ethylenoxide;

Castor oil or hydrogenated castor oil ethoxylated with from 5 to 60 mole ethylenoxide;

fatty acid sugar mono- or diester, especially ester of sucrose with one or two C8- to C30 or C12 to C22-fatty acid, INCI: Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate;

ethoxylated sorbitan esters such as ester of sorbitan with one, two or three C8- to C22-fatty acid and a degree of ethoxylation of from 4 to 20;

polyglyceryl fatty acid ester, especially of one, two or more C8- to C22-fatty acids with polyglycerol of preferably 2 to 20 glycerol units;

alkylglucoside, alkyloligoglucoside or alkylpolyglucoside with C8- to C22-alkyl groups, e.g., Decyl Glucoside or Lauryl Glucoside.

Anionic surfactants are, for example, alkyl carboxylic acids, alkyl ethersulfates, alkylsulfates, sulfosuccinates, fatty acid isethienates, phosphoric acid alkyl ester, ethoxylated phosphoric acid alkyl ester such as mono- di- or triesters of phosphoric acid with C8- to C22-fatty alcohols ethoxylated with 2 to 30 mol ethylenoxide, acylaminoacids, said acyl groups having preferably 8 to 30 carbon atoms. Preferred emulsifiers are triesters of phosphoric acid with ethoxylated fatty alcohols such as for example the triester of phosphoric acid with cetyl and stearyl alcohol ethoxylated with 4 mol of ethylenoxide (INCI: Triceteareth-4 Phosphate).

Solid Hair Styling Wax Products

In one embodiment of the method according to the present invention, the di- or oligosaccharide polyesters are used in solid hair styling wax products. These hair wax products according to the invention for treatment or preparation of a human hairstyle usually comprise a composition with a solid and wax-like consistency comprising at least one wax or wax-like substance. The compositions of the solid hair wax products according to the invention have a needle penetration number (measurement unit 0.1 mm, test weight 100 g, test duration 5 s, test temperature of 25° C., according to DIN 51 579) of preferably greater than or equal to 10, or 20 and preferably not more than 70. The wax or wax-like substance can be the di- or oligosaccharide polyester itself. In case the saccharide ester is liquid or oily, it is combined with at least one of the non-saccharide ester waxes mentioned above, for example paraffin waxes, bees wax and the like. The total amount of waxes and wax-like substances in solid styling wax products is preferably from about 5% to 60%, more preferably 10% to 50%, most preferably 20% to 50% by weight of the composition. The compositions of the solid hair styling waxes can additionally contain the liquid hydrophobic oils of the types and amounts mentioned above.

Hair Styling Creams or Soft Waxes

In another embodiment of the method according to the present invention, the di- or oligosaccharide polyesters are used in creamy, soft or semi-solid hair styling products. These hair wax products according to the invention for treatment or preparation of a human hairstyle usually comprise a composition with a creamy or semi-solid consistency comprising at least one oily substance. Cream products typically are emulsions of at least one hydrophobic oil and water in the presence of at least one emulsifier of the type and amounts mentioned above. The amount of water is preferably from about 10% to 70%, more preferably 20% to 60%, most preferably 30% to 50% by weight. The oily substance can be the di- or oligosaccharide polyester itself. In case the di- or oligosaccharide ester is solid or waxy, it is combined with at least one of the non-saccharide ester hydrophobic oils mentioned above, for example hydrocarbon oils such as paraffin oil or isoparaffin oil or silicon oils and the like. The total amount of oils in creamy or semi-solid styling products is preferably from about 5% to 60%, more preferably 10% to 55%, most preferably 15 to 50% by weight of the composition. The compositions of the creamy, soft or semi-solid hair styling products can additionally contain wax compounds of the types and amounts mentioned above.

Spray Wax Products and Foam Wax Products

In further embodiments of the method according to the present invention, the hair styling products are hair styling spray waxes and hair styling foam waxes. These products comprise a spraying device or a foaming device and a composition comprising at least one of the fully esterified di- or oligosaccharide polyesters described above. The spray or foam products can be aerosol products containing propellants or non-aerosol products without propellants. The compositions are sprayable or foamable and preferably liquid at room temperature. The composition comprises preferably at least one wax or wax-like substance. The wax or wax-like substance can be the di- or oligosaccharide polyester itself. In case the saccharide ester is liquid or oily, it is preferably combined with at least one of the non-saccharide ester waxes mentioned above, for example paraffin waxes, bees wax and the like. The total amount of waxes and wax-like substances in spray wax or foam wax products is preferably from about 5% to 60%, more preferably 10% to 50%, most preferably 15% to 50% by weight of the composition. The compositions of the spray wax or foam wax products can additionally contain the liquid hydrophobic oils of the types and amounts mentioned above. The compositions can contain easily volatilized hydrophobic substances which are liquid at room temperature and have a boiling point in the range of 30° C. to 100° C., preferably 35° C. to 70° C. Liquid hydrocarbons, liquid cyclic or linear silicones (dimethylpolysiloxanes), or mixtures of the foregoing materials, are suitable. Linear or branched alkanes with 5 to 7 carbon atoms are especially suitable hydrocarbons. Pentane is particularly preferred. Hexamethyldisiloxane is especially preferred as a liquid easily-volatilized silicone.

The non-aerosol spray or foam wax products comprise a container with a mechanical pumping device and a spray head or a foam head. The container for the non-aerosol spray wax product according to the invention can be made from any known material suitable for non-aerosol spray or foam products, in so far as the material is sufficiently pressure-resistant to slight increases in pressure if easily-volatilized hydrophobic substances are used and provides a sufficient barrier to diffusion of the ingredients of the composition contained in the container. Metals, such as aluminum or tin plate, or plastic are suitable materials. Transparent or at least translucent materials are preferred so that the product consistency and/or the amount of product left in the container is visible from the outside of the container. The product container is preferably made from glass or polyethylene terephthalate (PET). Commercially available pumps, spray heads and foam heads can be used with the container for the non-aerosol spray wax or foam wax product according to the invention. If a volatile hydrocarbon such as pentane is present in the composition contained in the container, then a spray pump, which is made from a material that is resistant to swelling in the presence of pentane, is preferred. This sort of material is for example polyoxymethylene (POM). One spray pump suitable according to the invention is, for example, the Seaquist-Perfect PZI/100 HVT fine spray pump. The spray pumps can have an aeration opening but this is not necessarily required if a volatile hydrocarbon is present in the composition.

The spray wax or foam wax product according to the invention can also be an aerosol product. Waxes having especially large surface areas (wax snows) can be made by using gaseous substances (propellant gases, such as propane, butane, and the like). These wax snows are easily processed and gently worked into the hair. The aerosol spray wax or foam wax products comprise a pressure resistant container with a spray cap or a foam cap and a sprayable or foamable composition according to the invention comprising at least one propellant contained in the pressure resistant container. The amount of propellant is preferably from about 5% to 60%, more preferably 10% to 50%, most preferably 20% to 40% by weight of the composition. The wax material of the composition is preferably dissolved or suspended in a liquified hydrophobic propellant gas. Typical waxes used in hair wax products are soluble or at least can be suspended in organic solvents. These solvents include easily volatilized alkanes, such as pentane and its isomers, which are liquid at normal pressures and at room temperature, as well as liquifiable propellant gases used in the aerosol products, such as propane, butane and its isomers. If a hair wax composition is dissolved or suspended together with one of these propellant gases and filled in an aerosol container, it may be sprayed either as a fine spray or as spray foam like wax snow. A dense wax snow (frozen wax) is produced, when one uses a foam head instead of a spray head. The dense wax snow arises by heat loss due to evaporation of the propellant gas. The foam-like or flake-like consistency with the larger wax surface area permits very easy distribution on the hands and in the hair.

Preferred propellants are liquified propellant gases which are gaseous at room temperature under normal pressure conditions and liquifiable under pressure at room temperature. Suitable propellant gases include propane, n-butane, isobutene, and fluorinated hydrocarbons, such as 1,1-difluoroethanes or 1,1,1,2-tetrafluoroethane or dimethyl ether. These propellant gases can be used alone or in a mixture, e.g., a mixture of propane and/or butane and dimethyl ether. A mixture of propane and butane is especially preferred. An easily volatilized hydrophobic substance can also be composed in addition to the propellant gas. This includes a material that is liquid at room temperature and which has a boiling point of from about 30° C. to 100° C., preferably from about 35° C. to 70° C. Liquid hydrocarbons, liquid cyclic or linear silicones (dimethylpolysiloxanes), or mixture of the foregoing materials, are especially suitable as volatile hydrophobic substances. Suitable hydrocarbons include linear or branched alkanes with 5 to 7 carbon atoms, especially pentane. For example, hexamethyldisiloxane is especially suitable as a liquid easily volatilized silicone.

The pressure-tight aerosol container for the aerosol spray wax product according to the invention can be made from known materials for aerosol products. Suitable materials include metals, such as aluminum or tin plate. Commercial spray heads and foam heads can be used for the aerosol containers for the aerosol spray wax and aerosol foam wax product according to the invention.

According to one embodiment of the invention, the hair styling products are colored products containing at least one colorant or color additive. Preferred product colors are oil soluble organic dyes. But insoluble pigments or water soluble or alcohol soluble dyes can also be used. The colored hair wax products preferably contain essentially no or only minor amounts (such as for example less than about 5%, preferably less than about 1% by weight) of non-white waxes such as carnauba wax which are colored by themselves. The amount of colorants can vary for example from about 0.0001% to 5% by weight. Colorants and color additives can for example be selected from those listed in the *International Cosmetic Ingredient Dictionary and Handbook*, 10th edition, 2004, volume 3, section 3 under the function "colorants".

Optional Ingredients

The composition according to the invention can also contain conventional cosmetic additives usually used in hair treatment compositions in addition to the above-mentioned ingredients, e.g., solvents, such as water or univalent or multivalent C1 to C5-alcohols, especially ethanol, propanol, glycerol or glycols, in an amount of, for example, up to 10% by weight, preferably from about 0.1% to 8% by weight, in creamy emulsions the amount of water can be higher (see above); fragrances and perfume oils in an amount of up to 2% by weight, preferably from about 0.01% to 1% by weight; preservatives such as for example parabenes, phenoxetol, iodopropynyl carbamate, parahydroxybenzoic acid ester, benzoic acid, salicylic acid, sorbic acid, mandelic acid, polyhexamethylene biguanidine hydrochloride or isothiazoline based compounds in an amount of, for example, up to 2% by weight, preferably 0.01% to 1% weight; hair care substances, such as, e.g., betaine, panthenol, plant extracts, vegetable extracts, protein hydroylsates and silk hydrolysates, lanolin derivatives, in an amount of, for example, 0.01% to 5%, preferably 0.1% to 4% by weight; pigments or pearlescent pigments in an amount of, for example, from about 0.01% up to 25% by weight, preferably 1% to 20% by weight, e.g., such as those with a titanium dioxide/mica base; film-forming polymers, such as polyvinyl pyrrolidone or vinylpyrrolidone/vinyl acetate copolymer in an amount of up to 5% by weight, preferably from 0.1% to 4% by weight; physiologically compatible silicone derivatives, such as volatile or non-volatile silicone oils or high molecular weight siloxane polymers in an amount of 0.05% to 20% by weight; light protective agents, antioxidants, radical-trapping agents, anti-dandruff agents, vitamines, luster-imparting substances and combability-improving substances in an amount of 0.01% to 2% by weight.

Method of Making

The compositions used in the method of the present invention can be made by conventional formulation and mixing techniques. Cream products in the form of emulsions can be made by emulsification of aqueous phase and oil phase, preferably done at elevated temperatures of for example 80° C. to 100° C. Volatile ingredients such as fragrances are added preferably at lower temperatures for example at 50° C. to 70° C. The emulsified composition is filled into the final packaging when still in a fluid state at temperatures above room temperature, for example at 50° C. to 70° C. The compositions become non-fluid after cooling to room temperature. The final packaging is preferably a transparent or translucent package. The solid or creamy hair wax product according to the invention can be made by melting the wax-like ingredients together and mixing with the other ingredients except volatile ingredients. Subsequently the mixture is cooled. Volatile compounds are added and mixed shortly before the mixture solidifies. The still flowing mass is filled in the desired container (cup or other container) prior to solidification. The spray wax or foam wax product according to the invention can be made by melting the waxy ingredients and mixing or dissolving them with the other ingredients and liquid substances, without the propellant. Subsequently the mixture is cooled to room temperature. This liquid solution or suspension is filled in the spray container. In the case of a non-aerosol product a mechanically operated pump device is provided. In the case of an aerosol product the propellant gas is supplied to the container. The container is then either provided with a spray head for producing a wax spray or with a foam head for producing a wax foam.

Method of Use

An embodiment of the invention is a method of hair treatment, said method comprising the steps of:

a) providing a hair styling product selected from hair styling waxes, hair styling creams, hair styling foam wax products, and hair styling spray wax products as described in detail above, said products comprising a composition containing at least one of above-mentioned fully esterified di- or oligosaccharide polyesters;

b) applying the composition to hair, preferably to dry hair; and c) setting or putting the hair in a hair style without subsequent rinsing.

Such method generally involves application of an effective amount of the product to dry, slightly damp, or wet hair preferably before the hair is arranged to a desired style. The composition is then dried or allowed to dry. By "effective amount" is meant an amount sufficient to provide the hair texture, hair shine, and style benefits desired considering the length and texture of the hair. In general, from about 0.5 g to about 50 g of product will be applied to the hair, depending upon the particular product formulation, length of hair, and type of hair style.

A specific embodiment of the invention for a hair root lifting application is a method of hair treatment, said method comprising the steps of:

a) providing a hair styling product selected from hair styling foam wax products and hair styling spray wax products as described in detail above, said products comprising a composition containing at least one of above-mentioned fully esterified di- or oligosaccharide polyesters in combination with a foaming device or a spraying device and b) spraying the composition directly onto the roots of the scalp hair.

Compositions of the type of the exemplary compositions described below will have benefits over conventional hair styling wax products, containing carnauba wax instead of the sucrose polyester, in one or more of whiteness of product color in case of uncolored products or color brightness in case of colored products; ease of distribution in hand; ease of working into hair; definition of hair; texture of hair; outstanding shine; relative low overloading of the hair; no or little visible residues on hair; reduced crumbling of the product mass; good formability of the hair style.

EXAMPLES

The compositions illustrated in the following examples illustrate specific embodiments of the hair styling compositions of the present invention, but are not intended to be limiting thereof. Other modifications can be undertaken by the skilled artisan without departing from the spirit and scope of this invention. These exemplified embodiments of the hair styling composition of the present invention provide styling and shine benefits with especially low loading of the hair. The compositions illustrated in the following examples are prepared by conventional formulation and mixing methods. All exemplified amounts are listed as weight percents and exclude minor materials such as diluents, preservatives, color solutions, imagery ingredients, botanicals, and so forth, unless otherwise specified. If a trade name is mentioned as ingredient and the respective product is itself a mixture (e.g., a solution, emulsion, dispersion. etc.), then the exemplified amount relates to this mixture, unless otherwise specified.

Example 1

Curl Wax

| | |
|---|---|
| 10 | Triceteareth-4 Phosphate |
| 10 | Ceresin |
| 2 | Bees wax |
| 30 | Paraffin oil |
| 3 | Sucrose polybehenate (SEFA ® Behenate) |
| 0.4 | Fragrance |
| 0.3 | Propyl parabene |
| 0.3 | Methyl parabene |
| 1 | Phenoxetol |
| balance to 100 | Water |

Example 2

Solid Wax

| A | B | |
|---|---|---|
| 46.2 | 46.2 | Paraffin oil |
| 25 | 25 | Ceresin |
| 10 | 10 | Triceteareth-4 Phosphate |
| 10 | — | Sucrose polybehenate (SEFA ® Behenate) |
| — | 10 | Carnauba wax |
| 5 | 5 | Bees wax |
| 3 | 3 | PEG-25 hydrogenated castor oil |
| 0.3 | 0.3 | Fragrance |
| 0.2 | 0.2 | Propyl parabene |
| 0.2 | 0.2 | Ethylhexyl methoxycinnamate |
| 0.1 | 0.1 | Panthenol |

Composition A according to the invention has been compared with comparative ion B. Benefits have been found according to the following criteria:

| | |
|---|---|
| consistency: | A better than B, which is crumbling, less homogeneous and less smooth |
| distribution in the hands: | A better than B |
| formability of hair: | A better than B |
| definition of hair | A better than B |
| shine of hair | A better than B |
| feeling of hair | A better than B, which is more sticky and less smooth |
| optical appearance in the jar | A: white; B: yellowish/brownish |

Example 3

Aerosol Wax

| | |
|---|---|
| 8 | Triceteareth-4 Phosphate |
| 25 | Ceresin |
| 40 | Paraffin oil |
| 10 | Sucrose polybehenate (SEFA ® Behenate) |
| 0.4 | Fragrance |

-continued

| | |
|---|---|
| 1.6 | PEG-40 hydrogenated castor oil |
| 20 | Pentane |

The ingredients of the composition are filled into an aerosol can. The base composition is charged with propane/butane (2.7 bar) in a weight ratio of 30% propellant to 70% base composition. The can is provided with either a commercial spray cap or a commercial foam head.

Example 4

Wax Cream

| | |
|---|---|
| 10 | Triceteareth-4 Phosphate |
| 10 | Ceresin |
| 3 | Bees wax |
| 30 | Paraffin oil |
| 4 | Sucrose polybehenate (SEFA ® Behenate) |
| 0.3 | Fragrance |
| 0.3 | Propyl parabene |
| 0.3 | Methyl parabene |
| 1 | Phenoxetol |
| balance to 100 | Water |

Example 5

Soft Wax

| | |
|---|---|
| 8 | Triceteareth-4 Phosphate |
| 20 | Ceresin |
| 4 | Bees wax |
| 40 | Paraffin oil |
| 10 | Sucrose polybehenate (SEFA ® Behenate) |
| 4 | Silicone oil (liquid polydimethylsiloxane) |
| 9 | Ethanol |
| 0.2 | PEG-25 PABA |
| 0.3 | Panthenol |
| 0.4 | Fragrance |
| 0.3 | Propyl parabene |
| 1 | Phenoxetol |

Example 6

Curl Wax

| | |
|---|---|
| 10 | Triceteareth-4 Phosphate |
| 10 | Ceresin |
| 2 | Bees wax |
| 30 | Paraffin oil |
| 3 | Sucrose polycottonseedate (SEFA ® Cottonate) |
| 0.4 | Fragrance |
| 0.3 | Propyl parabene |
| 0.3 | Methyl parabene |
| 1 | Phenoxetol |
| balance to 100 | Water |

Example 7

Solid Wax

| | |
|---|---|
| 10 | Triceteareth-4 Phosphate |
| 25 | Ceresin |
| 6 | Bees wax |
| 47 | Paraffin oil |
| 10 | Sucrose polycottonseedate (SEFA ® Cottonate) |
| 0.4 | Fragrance |
| 0.3 | Propyl parabene |
| 1 | Phenoxetol |

Example 8

Aerosol Wax

| | |
|---|---|
| 8 | Triceteareth-4 Phosphate |
| 20 | Ceresin |
| 40 | Paraffin oil |
| 10 | Sucrose polycottonseedate (SEFA ® Cottonate) |
| 0.4 | Fragrance |
| 1.6 | PEG-40 hydrogenated castor oil |
| 20 | Pentane |

The ingredients of the composition are filled into an aerosol can. The base composition is charged with propane/butane (2.7 bar) in a weight ratio of 30% propellant to 70% base composition. The can is provided with either a commercial spray cap or a commercial foam head.

Example 9

Wax Cream

| | |
|---|---|
| 10 | Triceteareth-4 Phosphate |
| 10 | Ceresin |
| 3 | Bees wax |
| 30 | Paraffin oil |
| 4 | Sucrose polycottonseedate (SEFA ® Cottonate) |
| 0.3 | Fragrance |
| 0.3 | Propyl parabene |
| 0.3 | Methyl parabene |
| 1 | Phenoxetol |
| balance to 100 | Water |

Example 10

Soft Wax

| | |
|---|---|
| 8 | Triceteareth-4 Phosphate |
| 20 | Ceresin |
| 4 | Bees wax |
| 40 | Paraffin oil |
| 10 | Sucrose polycottonseedate (SEFA ® Cottonate) |
| 4 | Silicone oil (liquid polydimethylsiloxane) |
| 9 | Ethanol |

-continued

| | |
|---|---|
| 0.2 | PEG-25 PABA |
| 0.3 | Panthenol |
| 0.4 | Fragrance |
| 0.3 | Propyl parabene |
| 1 | Phenoxetol |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed a "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of hair treatment, said method comprising the steps of:
    a) providing a hair styling product selected from hair styling foam wax products and hair styling spray wax products, said products comprising a composition comprising:
        i) from about 5% to 50% by weight of bees wax or ceresin
        ii) from about 1% to 15% by weight of sucrose polybehenate or sucrose polycottonseedate
        iii) from 5% to 60% by weight of silicone oil or mineral oil
        iv) from about 0.5% to 20% by weight of emulsifier, wherein the emulsifier is ethoxylated hydrogenated castor oil in combination with a foaming device or a spraying device and
    b) spraying the composition directly onto the roots of the scalp hair.

* * * * *